United States Patent
Frigg et al.

[11] Patent Number: 5,180,382
[45] Date of Patent: Jan. 19, 1993

[54] BONE SCREW

[75] Inventors: Robert Frigg, Davos-Platz; Stephan Perren, Davos-Dorf; Martin Allgöwer, Reinach; Paul Gisin, Waldenburg, all of Switzerland

[73] Assignee: Synthes (U.S.A.), Paoli, Pa.

[21] Appl. No.: 808,594

[22] Filed: Dec. 17, 1991

[30] Foreign Application Priority Data

Dec. 19, 1990 [DE] Germany .................. 9017101

[51] Int. Cl.⁵ .............................................. A61B 17/56
[52] U.S. Cl. ................................ 606/65; 606/72; 606/73
[58] Field of Search ............. 606/65, 66, 67, 68, 606/72, 73, 75

[56] References Cited

U.S. PATENT DOCUMENTS

| | | | |
|---|---|---|---|
| 2,382,019 | 8/1945 | Miller | 606/72 |
| 3,915,162 | 10/1975 | Miller | 606/73 |
| 4,175,555 | 11/1979 | Herbert | 606/73 |
| 4,456,005 | 6/1984 | Lichty | 606/73 |
| 4,463,753 | 8/1984 | Gustilo | 606/73 |
| 4,468,200 | 8/1984 | Münch | 606/73 |
| 4,537,185 | 8/1985 | Stednitz | 606/73 |
| 4,640,271 | 2/1987 | Lower | 606/73 |
| 4,723,541 | 2/1988 | Reese | 606/73 |
| 4,940,467 | 7/1990 | Tronzo | 606/73 |
| 5,019,078 | 5/1991 | Perren | 606/73 |

*Primary Examiner*—Michael A. Brown
*Attorney, Agent, or Firm*—Davis Hoxie Faithfull & Hapgood

[57] ABSTRACT

A bone screw (1) has a screw head (2), a screw tip (11), and a shaft (5) with a thread (8,14). The threaded segment (6,7) of the shaft (5) has a head-end, essentially cylindrical first shaft section (6) with minor diameter $d_1$ (16), and a tip-end second shaft segment (7) that is connected with the first shaft segment (6) and which has a smaller minor diameter $d_2$ (17). The thread (8,14) in the two shaft segments (6,7) has the same pitch (10,12).

21 Claims, 2 Drawing Sheets

BONE SCREW

FIELD OF THE INVENTION

The invention relates to a bone screw for orthopedic use.

BACKGROUND OF THE INVENTION

Bone screws of the type here involved can be used for anchoring external setting components on the bone, e.g. when an external fixation device is used in osteosynthesis. In this indication, bone screws are used within a framework of one or more longitudinal members.

Bone screw according to the invention may be used in the form of Schanz screw, which serves to anchor external setting components in the bone. The Schanz screws are inserted through small incisions in the skin and the soft tissue into the bone. The thread of the Schanz screw prevents axial slippage of the screw in the bone hole. The actual setting component, the external fixation device, is mounted on the normally smooth shaft of the Schanz screw. The principal area of this second indication is that of open fractures. These fractures cannot be handled by internal osteosynthesis, since the implantation would cause additional damage to the soft parts. A disadvantage of this known method, however, is the permanent linking of the bone with the "outside world" through the transcutaneously applied Schanz screws. The longer these Schanz screws are left in the body, the greater the danger of a "pintrak infection." Such an infection is aggravated by the Schanz screws, which are not under tension, because these screws promote bone resorption by micro movements. In an extreme case, such loosening can lead to a sequestration. Clinical research has shown that a pintrak infection would occur very rarely if the screw were well anchored in the bone.

In EP-A2 0 369 266 a bone screw is disclosed which between a smooth shaft part and a threaded part, has a shoulder with appropriate slope so that a radial pre-tension is created upon implantation in a tubular bone. In this known bone screw, the introduction of the screw shaft with its enlarged diameter into the proximal corticalis of the tubular bone is disadvantageous. If the thread at the end does not have an adequate hold in the counter-corticalis, the anchoring will not be sufficient to draw the conical expanding screw shaft into the proximal corticalis. In such a case the threading is torn out, and it is no longer possible to screw the screw into the bone by axial pressure. Another problem with this known screw resides in maintaining the hole diameter tolerance during drilling into the proximal corticalis. If the drill is not guided properly, an excessively large hole is created that cannot be radially pre-stressed sufficiently.

SUMMARY OF THE INVENTION

The present invention provides a bone screw designed to overcome these problems. The bone screw according to the invention provides. an insertion in which the bone screw can be permanently screwed into an under-dimensioned hole without damage to the bone, with a single drilling procedure, with precisely controlled radial compression of the receiving bone tissue, and with maintenance of the radial pressure over the entire circumference even under additional functional loads.

In accordance with the invention these goals are met by means of a bone screw having a head end, a tip end and a shaft extending between said ends, said shaft having a first threaded segment toward the head end, with a minor diameter $d_1$ and a second threaded segment towards the tip end with a minor diameter $d_2$, $d_2$ being less than $d_1$, the thread in said segments having the same pitch. Preferably a third transition segment is provided between the first and second segments.

The anatomical distance separating the bone fragments, predetermined for screw insertion, is maintained when the bone screw is screwed in. A bone-free cavity existing between the bone pieces is thereby securely bridged. The transitional sequent in this embodiment is preferably shorter than or equal to one pitch of the thread, which appropriately is designed to be self-cutting, so that the operator can insert the bone screw directly after the positioning of the necessary hole.

Advantageously, the transitional area between the two threaded sequences is continuously tapered, e.g. in the form of a cone.

In preferred embodiment the shaft has an additional, smooth, fourth shaft section, connected at its head end to the first threaded segment.

BRIEF DESCRIPTION OF THE DRAWINGS

The invention will be further described with reference to the accompanying drawings, in which.

DETAILED DESCRIPTION OF THE INVENTION

Figure 1:
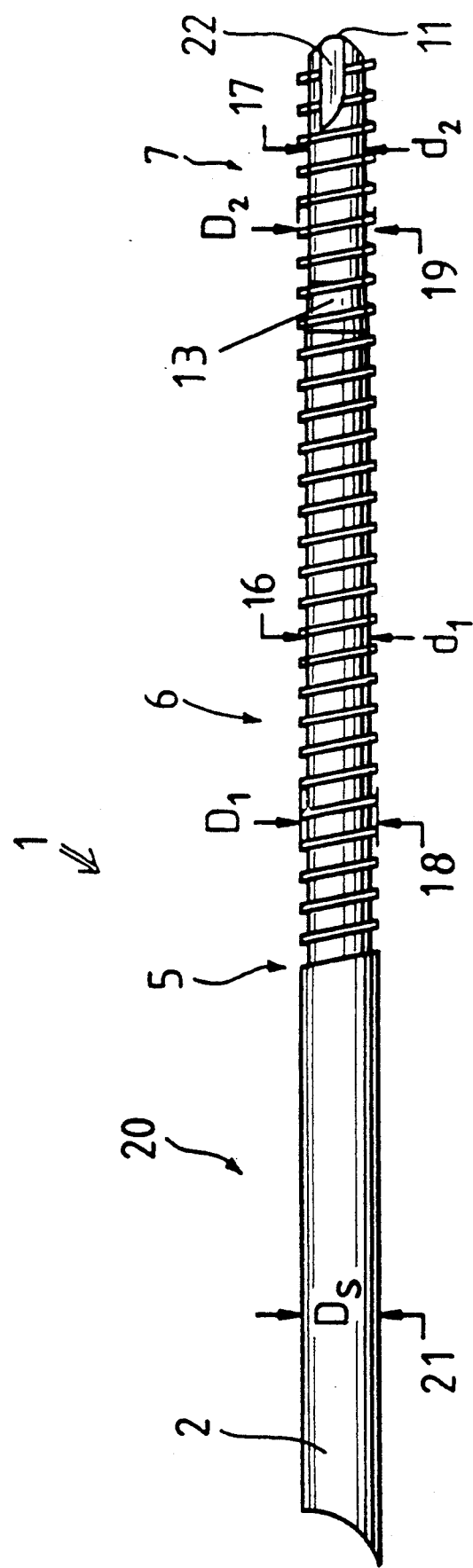
FIG. 1 is a view in side elevation of a preferred embodiment of the bone screw according to the invention.
Figure 2:
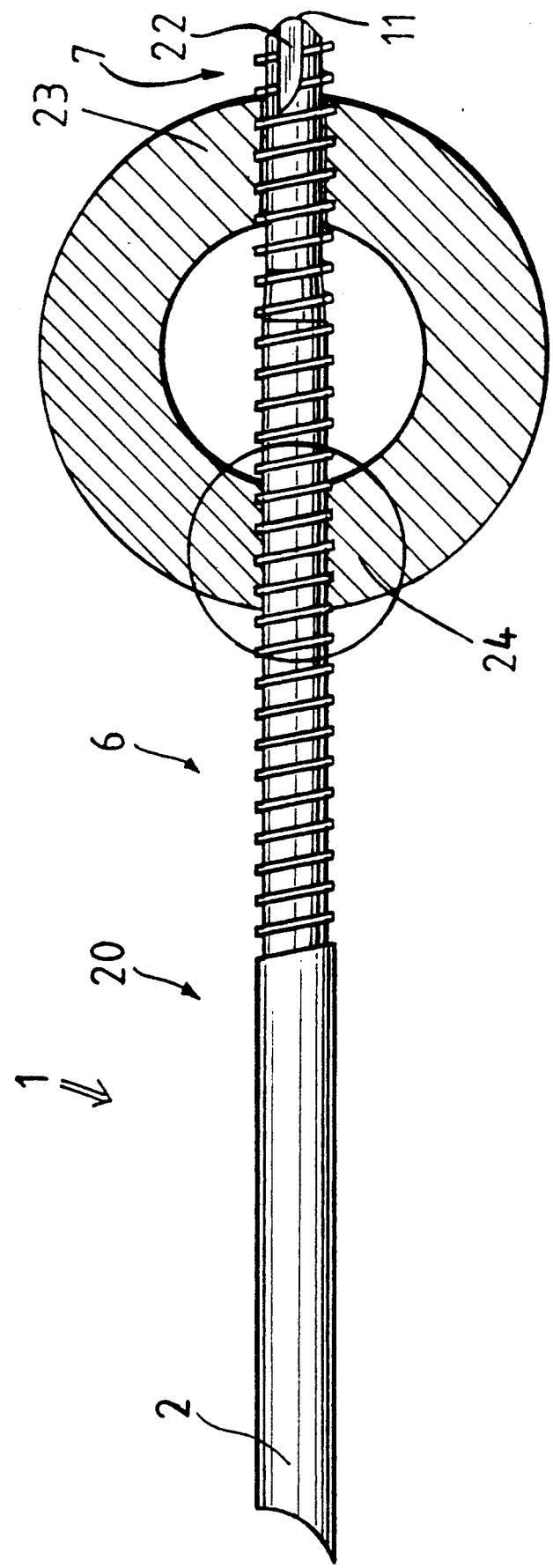
FIG. 2 is schematic view of bone screw of FIG. 1 implanted in a tubular bone.

A preferred embodiment of a bone screw according to the invention is shown in FIGS. 1 and 2. The bone screw 1 illustrated in FIG. 1 consists essentially of screw head 2, shaft 5, and screw tip 11. Shaft 5 has a head-end, smooth shaft segment 20 and a threaded segment 6,7. Segment 6,7 consists of a head-end segment 6 having a minor diameter 16 $d_1$ and a shorter tip-end shaft segment 7 having a minor diameter 17 $d_2$. The two threaded shaft segments 6 and 7 are connected through a transitional area 13 with a conically tapered diameter. In this embodiment, the conical transitional area 13 decreases continuously from minor diameter d to minor diameter $d_2$. The major diameter 19 $D_2$ of the threaded tip-end second shaft segment 7, and the diameter 21 ($D_s$) of smooth shaft segment 20, may be the same.

The length of the first shaft section of the shaft is dependent on the absolute dimensions of the bone screw. The increase in the thread pitch of the thread of the second shaft section is advantageously between 1.5 and 2 mm, preferably between 1.7 and 1.8 mm.

Referring to the dimensions of the embodiment of FIGS. 1 and 2, the length of the first section is typically between about 60 and about 80 mm., preferably between about 65 and 75 mm. The length of the transitional area is advantageously from about 3 to about 7 mm., and preferably from about 4 to about 6 mm. Since the fault expansion of the bone is around two to three per cent, the dimensions of the transition area in this embodiment should be selected in such manner that the ratio $d_1-d_2/d_2$ is between 0.004 and 0.020, preferably between 0.008 and 0.012. An optimal compression of the bone material can thereby be achieved.

Appropriately, the second, tip-end shaft section has a major thread diameter of $D_2$, which corresponds to the diameter $D_s$ of the fourth, head-end shaft section.

In addition, the screw tip is designed preferably to be self-cutting, e.g. in the form of a trocar or one or more cutting grooves radially distributed over the circumference. Appropriately, the threading of the bone screw has dimensions such that the ratio between the minor diameter $d_2$ and the major diameter $D_2$ of the second shaft section ranges between 0.89 and 0.95, preferably between 0.91 and 0.93.

To prevent the tip-end section of the thread segment from acting on the rear corticalis and the transitional segment from acting on the forward corticalis, both at the same time, which would lead to loss of control when the bone screw is screwed in, it is advantageous to have the transitional area at a distance of 15–25 mm, and preferably 18–22 mm, from the screw tip; its length depends on the absolute dimensions of the bone screw, and typically is between 3 and 7 mm, preferably between 4 and 6 mm.

In a typical screw of the type shown in FIGS. 1 and 2 the segment 6 is 70 mm. long and, the segment 7, 20 mm. The segment 6 has a minor diameter $d_1$, of 4.65 mm. and the segment 7 a minor diameter, $d_2$ of 4.60 mm. The conical transitional segment is 5 mm. long and tapers conically from 4.65 mm. to 4.60 mm. The transitional segment is 20 mm. from the screw tip 11. The major diameter $D_1$ of the threaded segment 7 is 5.0 mm. which is also the diameter $D_s$ of the smooth segment 20. The pitch of the thread of segment 7 is 1.75 mm.

The advantages achieved through the embodiment of FIGS. 1 and 2 are essentially that, thanks to the slightly different size of the shaft section with threading, a desired radial pre-stress is created in the bone hole, which pre-stress is at least partially maintained in the bone screw according to the invention even in case of additional functional loads, so that no relaxation with consequent resorption of the bone tissue occurs; in addition, only a single-step drill need be used in order for the two-stage core of the threaded section of the bone screw according to the invention to enter the bone hole permanently with a radial pre-stress but without injury to the bone.

Since the radial pre-stress in the bone screw according to the invention is implemented in the form of an over-sized thread, the height thereof is precisely defined by the minor diameter of the thread.

Screw tip 11 of bone screw 1 is designed to be self-cutting, and for that purpose has several radial cutting grooves 22 distributed over its circumference; it can also be designed as a trocar tip. The cutting media serve to expand the hole in the bone precisely to the minor diameter of bone screw 1, and additionally to cut the thread in the bone. For this reason, the diameter of the core hole in the bone can be slightly smaller without consequential unintended radial pre-stress when the bone screw 1 is implanted. If the exact core hole diameter were to be drilled for the core hole, there would be a danger of an excessive hole diameter being created by the surgeon through inaccurate drilling. The use of an over-dimensioned core hole diameter and the self-cutting screw tip 11 offer the additional advantage of achieving a "reamer effect," in which the hole made in the proximal corticalis by the self-cutting screw tip 11 corresponds exactly to the required starting diameter for the subsequent radial pre-stress.

As indicated in FIG. 2, the positioning of the bone screw 1 according to the invention is done by a one-step drilling of the tubular bone 23,24 with a common drill having a diameter of 4.5 mm, which, experience has shown, creates a hole diameter of 4.55 mm. Bone screw 1 with its tip-end shaft segment 7 is now inserted into this core hole with the customary tools. Since the minor diameter $d_2$ of tip-end shaft segment 7 of thread segment 6,7 is only 4.60 mm, practically no radial pre-stress is created in the rear corticalis 23.

Only when the head-end shaft segment 6 of thread segment 6,7 with minor diameter $d_1$ is screwed via the conical transitional section 13 into the forward corticalis is there a radial pre-stress of 0.05 mm, and the end result is as illustrated in FIG. 2.

What we claim is:

1. A bone screw having a screw head at one end, a tip at the other end and a shaft between the head and tip, said shaft having a first threaded segment at the head end with a major diameter $D_1$ and a minor diameter $d_1$ and a second threaded segment at the tip end with a major diameter $D_2$ and a minor diameter $d_2$, $d_2$ being less than $d_1$, the thread in said segments having the same pitch, and the ratio $(d_1 - d_2)/d_2$ being between about 0.004 and about 0.020.

2. The bone screw claimed in claim 1, and comprising a transitional segment between the first and second segments.

3. The bone screw claimed in claim 2, wherein the transitional segment tapers from minor diameter $d_1$ to minor diameter $d_2$.

4. The bone screw claimed in claim 2 wherein the transitional segment is positioned at a distance from about 15 to about 25 mm. from the screw tip.

5. The bone screw claimed in claim 4 wherein the distance is between about 18 and about 22 mm.

6. The bone screw claimed in claim 2 wherein the transition segment is between about 3 and about 7 mm. long.

7. The bone screw claimed in claim 6 wherein the transitional segment is between about 4 and about 6 mm. long.

8. The bone screw claimed in claim 1 wherein the thread is self-cutting.

9. The bone screw claimed in claim 1, wherein the major diameter of the thread of the second shaft segment is smaller than the minor diameter of the thread of the first shaft segment.

10. The bone screw claimed in claim 1 and comprising a smooth shaft segment between the head end and the first threaded segment.

11. The bone screw claimed in claim 1 wherein the ratio is between about 0.008 and about 0.012.

12. The bone screw claimed in claim 1 wherein second shaft segment major thread diameter $D_2$ corresponds to the diameter $D_s$ of the smooth shaft segment.

13. The bone screw claimed in claim 1 wherein the screw tip is self-cutting.

14. The bone screw claimed in claim 13 wherein the tip has the form of a trocar.

15. The bone screw claimed in claim 13 wherein the tip has a radial cutting groove.

16. The bone screw claimed in claim 1 wherein the ratio between minor diameter dz and the major diameter $D_2$ of the second threaded shaft segment is between about 0.89 and about 0.95.

17. The bone screw claimed in claim 16 wherein the ratio is between about 0.91 and about 0.93.

18. The bone screw claimed in claim 1 wherein the first shaft segment of the shaft is between about 60 and about 80 mm. long.

19. The bone screw claimed in claim 18 wherein the first shaft segment is between about 65 and about 75 mm. long.

20. The bone screw claimed in claim 1 wherein the pitch of the thread of the second shaft segment is between about 1.5 and about 2 mm.

21. The bone screw claimed in claim 20 wherein the pitch is between about 1.7 and about 1.8 mm.

* * * * *

UNITED STATES PATENT AND TRADEMARK OFFICE
CERTIFICATE OF CORRECTION

PATENT NO. : 5,180,382

DATED : January 19, 1993

INVENTOR(S) : Frigg, et. al.

It is certified that error appears in the above-identified patent and that said Letters Patent is hereby corrected as shown below:

Col. 2, line 48     change "d" to --$d_1$--.

Col. 4, line 64     (claim 16) change "dz" to --$d_2$--.

Signed and Sealed this

Thirtieth Day of November, 1993

Attest:

BRUCE LEHMAN

Attesting Officer     Commissioner of Patents and Trademarks